United States Patent [19]
Garst et al.

[11] Patent Number: 5,674,910
[45] Date of Patent: Oct. 7, 1997

[54] 7-(5-SUBSTITUTED CYCLOPENTYL) AND (5-SUBSTITUTED CYCLOPENTENYL) HEPTYL ALCOHOLS, HEPTYLAMINES AND HEPTANOIC ACID AMIDES, AND METHOD OF LOWERING INTRAOCULAR PRESSURE IN THE EYE OF A MAMMAL BY ADMINISTRATION OF THESE NOVEL COMPOUNDS

[75] Inventors: Michael E. Garst, Newport Beach; Robert M. Burk, Irvine, both of Calif.

[73] Assignee: Allergan, Waco, Tex.

[21] Appl. No.: 572,437

[22] Filed: Dec. 14, 1995

Related U.S. Application Data

[62] Division of Ser. No. 355,463, Dec. 14, 1994, Pat. No. 5,524,431, which is a division of Ser. No. 964,223, Oct. 21, 1992, Pat. No. 5,385,945.

[51] Int. Cl.[6] .................... C07C 405/00; A61K 31/557
[52] U.S. Cl. ............................. 514/659; 564/454
[58] Field of Search ..................... 564/454; 514/659

[56] References Cited

U.S. PATENT DOCUMENTS

| | | | |
|---|---|---|---|
| 3,935,261 | 1/1976 | Caton | 564/189 |
| 4,054,604 | 10/1977 | Bernady | 564/189 |
| 4,058,564 | 11/1977 | Smith | 508/838 |
| 4,256,745 | 3/1981 | Skuballa | 508/838 |
| 4,454,339 | 6/1984 | Skuballa, II | 564/189 |
| 4,599,353 | 7/1986 | Bito | 514/530 |
| 4,994,274 | 2/1991 | Chan et al. | 424/427 |
| 5,034,413 | 7/1991 | Chan et al. | 514/530 |
| 5,385,945 | 1/1995 | Garst et al. | 514/613 |

FOREIGN PATENT DOCUMENTS

| | | | |
|---|---|---|---|
| 0242580 | 10/1987 | European Pat. Off. | A61K 31/557 |
| 0364417 | 4/1990 | European Pat. Off. | A61K 31/557 |
| 2312240 | 12/1976 | France | A61K 31/21 |
| 2386523 | 3/1978 | France | C07C 177/00 |
| 2629834 | 1/1978 | Germany | 564/189 |
| 8810252 | 12/1988 | WIPO | C07C 177/00 |
| 9003170 | 4/1990 | WIPO | A61K 31/557 |
| 9213835 | 8/1992 | WIPO | C07C 405/00 |

OTHER PUBLICATIONS

Bito, L. Z., *Arch. Ophthalmol, 105*, 1036 (1987).
Bito, L. Z., *Applied Pharmacology in the Medical Treatment of Glaucomas*, Drance, S.M. and Neufeld, A.H. eds., New York, Grune & Stratton, 1984 pp. 477–505).
Bito, L. Z., *Biological Protection with Prostaglandins*, Cohen, M.M., ed., Boca Raton Fla. CRC Press Inc., 1985, pp. 231–252.
M.S. Starr, *Exp. Eye Res.* 11, 170–177 (1971).
Nilsson et al., *Invest, Ophthalmol. Vis. Sci.* 28 (suppl), 284 (1987).
Siebold et al., *Prodrug 5*, 3 (1989).
Woodward, et al., Prostaglandin $F_{2\alpha}$Effects on Intraocular Pressure Negatively Correlate with FP–Receptor Stimulation, *Investigative Ophthalmology & Visual Science*, vol. 30, No. 8, Aug. 1989.
Zajacz, et al., Effect on Human Eye of Prostaglandin and a Prostaglandin Analogue Used to Induce Abortion, The Eye: Reproduction, *Obstetrics and Gynecology*, 4, 316 (1976).
Database Biosis Biosciences Information, Service Philadelphia, PA, U.S. AN=7925460, Invest. Ophthalmol, Visual Sci., vol. 32 No. 4, 1991, p. 1257, Woodward D.F., et al. "Marked Species Differences in The Pharmacology of Prostanoid Induced Ocular Hypotension".
Cohen, M. M., ed. Boca Raton Fla. CRC Press Inc., 1985, 231–252.

*Primary Examiner*—Robert Gerstl
*Attorney, Agent, or Firm*—Gabor L. Szekeres; Robert J. Baran; Martin A. Voet

[57] ABSTRACT

Compounds of the formula

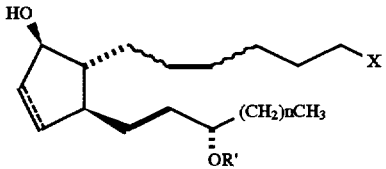

where the dotted line represents a bond or the absence of a bond, the wavy lines represent bonds which are either in cis or trans configuration; $R_1$ represents H, or CO—$R_2$ where $R_2$ is lower alkyl of 1 to 6 carbons, carbocyclic aryl or heterocyclic aryl; or carbocyclic aryl or heteroaryl substituted lower alkyl group; X represents CO—$NR_3R_4$, $CH_2OH$, $CH_2OR_5$, $CH_2O$—$COR_6$, and $CH_2$—$NR_3R_4$, where $R_3$ and $R_4$ independently are H or lower alkyl, $R_5$ is lower alkyl of 1 to 6 carbons, and $R_6$ is lower alkyl of 1 to 6 carbons, carbocyclic aryl or heterocyclic aryl; or carbocyclic aryl or heteroaryl substituted lower alkyl group, and n is an integer between 0 and 8 are capable of lowering intraocular pressure in the eye of a mammal.

19 Claims, No Drawings

7-(5-SUBSTITUTED CYCLOPENTYL) AND (5-SUBSTITUTED CYCLOPENTENYL) HEPTYL ALCOHOLS, HEPTYLAMINES AND HEPTANOIC ACID AMIDES, AND METHOD OF LOWERING INTRAOCULAR PRESSURE IN THE EYE OF A MAMMAL BY ADMINISTRATION OF THESE NOVEL COMPOUNDS

CROSS-REFERENCE TO RELATED APPLICATION

The present application is a divisional of application Ser. No. 08/355,463, filed on Dec. 14, 1994, now U.S. Pat. No. 5,524,431 which was a divisional of Ser. No. 07/964,223, filed on Oct. 21, 1992, now U.S. Pat. No. 5,385,945.

FIELD OF THE INVENTION

The present invention relates to 7-(5-substituted cyclopentyl) and (5-substituted cyclopentenyl) heptyl alcohols, heptyl amines and heptanoic acid amides, which are structurally related to certain prostaglandins. The present invention also relates to methods of administering said novel compounds to mammals for the purpose of lowering intraocular pressure in the mammalian eye.

BACKGROUND OF THE INVENTION

Ocular hypotensive agents are useful in the treatment of a number of various ocular hypertensive conditions, such as post-surgical and post-laser trabeculectomy ocular hypertensive episodes, glaucoma, and as presurgical adjuncts.

Glaucoma is a disease of the eye characterized by increased intraocular pressure. On the basis of its etiology, glaucoma has been classified as primary or secondary. For example, primary glaucoma in adults (congenital glaucoma) may be either open-angle or acute or chronic angle-closure. Secondary glaucoma results from pre-existing ocular diseases such as uveitis, intraocular tumor or an enlarged cataract.

The underlying causes of primary glaucoma are not yet known. The increased intraocular tension is due to the obstruction of aqueous humor outflow. In chronic open-angle glaucoma, the anterior chamber and its anatomic structures appear normal, but drainage of the aqueous humor is impeded. In acute or chronic angle-closure glaucoma, the anterior chamber is shallow, the filtration angle is narrowed, and the iris may obstruct the trabecular meshwork at the entrance of the canal of Schlemm. Dilation of the pupil may push the root of the iris forward against the angle, and may produce pupillary block and thus precipitate an acute attack. Eyes with narrow anterior chamber angles are predisposed to acute angle-closure glaucoma attacks of various degrees of severity.

Secondary glaucoma is caused by any interference with the flow of aqueous humor from the posterior chamber into the anterior chamber and subsequently, into the canal of Schlemm. Inflammatory disease of the anterior segment may prevent aqueous escape by causing complete posterior synechia in iris bombe and may plug the drainage channel with exudates. Other common causes are intraocular tumors, enlarged cataracts, central retinal vein occlusion, trauma to the eye, operative procedures and intraocular hemorrhage.

Considering all types together, glaucoma occurs in about 2% of all persons over the age of 40 and may be asymptotic for years before progressing to rapid loss of vision. In cases where surgery is not indicated, topical B-adrenoreceptor antagonists have traditionally been the drugs of choice for treating glaucoma.

Postagladins were earlier regarded as potent ocular hypertensives; however, evidence accumulated in the last two decades shows that some prostagladins are highly effective ocular hypotensive agents and are ideally suited for the long-term medical management of glaucoma. (See, for example, M. S. Starr, *Exp. Eye Res.* 11, 170–177, (1971); Bito, L. Z. *Biological Protection with Prostaglandisn* Cohen, M. M., ed., Boca Raton, Fla. CRC Press Inc., 1985, pp. 231–252; and Bito, L. Z., *Applied Pharmacology in the Medical Treatment of Glaucomas* Drance, S. M. and Neufeld, A. H. eds., New York, Grune & Stratton, 1984, pp. 477–505). Such prostagladins include $PGF_{2\alpha}$, $PGF_{1\alpha}$, $PGE_2$, and certain lipid-soluble esters, such as $C_1$ to $C_5$ alkyl esters, e.g. 1-isopropyl ester, of such compounds.

In the U.S. Pat. No. 4,599,353 certain prostaglandins, in particular $PGE_2$ and $PGF_{2\alpha}$ and the $C_1$ to $C_5$ alkyl esters of the latter compound, were reported to possess ocular hypotensive activity and were recommended for use in glaucoma management.

Although the precise mechanism is not yet known, recent experimental results indicate that the prostaglandin-induced reduction in intraocular pressure results from increased uvecscleral outflow [Nilsson et al., *Invest, Ophthalmol. Vis. Sci.* 28 (suppl), 284 (1987)].

The isopropyl ester of $PGF_{2\alpha}$ has been shown to have significantly greater hypotensive potency than the parent compounds, which was attributed to its more effective penetration through the cornea. In 1987 this compound was described as "the most potent ocular hyptensive agent ever reported." [See, for example, Bito, L. Z., *Arch. Ophthalmol,* 105, 1036 (1987), and Siebold et al., *Prodrug* 5, 3 (1989)].

Whereas prostagladins appear to be devoid of significant intraocular side effects, ocular surface (conjunctival) hyperemia and foreign-body sensation have been consistently associated with the topical ocular use of such compounds, in particular $PGF_{2\alpha}$ and its prodrugs, e.g. its 1-isopropyl ester, in humans. The clinical potential of postaglandins in the management of conditions associated with increased ocular pressure, e.g. glaucoma, is greatly limited by these side effects.

Certain phenyl and phenoxy mono, tri and tetra nor prostaglandins and their 1-esters are disclosed in European Patent Application 0,364,417 as useful in the treatment of glaucoma or ocular hypertension.

In a series of co-pending United States patent applications assigned to Allergan, Inc. prostaglandin esters with increased ocular hypotensive activity accompanied with no or substantially reduced side-effects are disclosed. The co-pending U.S. Ser. No. 386,835 (filed 27 Jul. 1989), relates to certain 11-acyl-prostaglandins, such as 11-pivaloyl, 11-acetyl, 11-isobutyryl, 11-valeryl, and 11-isovaleryl $PGF_{2\alpha}$. Intraocular pressure reducing 15-acyl prostaglandins are disclosed in the co-pending application U.S. Ser. No. 357,394 (filed 25 May 1989). Similarly, 11,15-9,15-and 9,11-diesters of prostaglandins, for example 11,15-dipivaloyl $PGF_{2\alpha}$ are known to have ocular hypotensive activity. See the co-pending patent applications U.S. Ser. No. 385, 645 filed 27 Jul. 1990, now U.S. Pat. No. 4,494,274; 584,370 which is a continuation of U.S. Ser. No. 386,312, and 585,284, now U.S. Pat. No. 5,034,413 which is a continuation of U.S. Ser. No. 395,834, where the parent applications were filed on 27 Jul. 1989. The disclosures of these patent applications are hereby expressly incorporated by reference.

3

SUMMARY OF THE INVENTION

Novel compounds of the present invention are shown in Formula 1

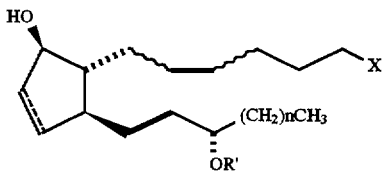

Formula 1 where the dotted line represents a bond or the absence of a bond, the wavy lines represent bonds which are either in cis or trans configuration;

$R_1$ represents H, or CO—$R_2$ where $R_2$ is lower alkyl of 1 to 6 carbons, carbocyclic aryl or heterocyclic aryl; or carbocyclic aryl or heteroaryl substituted lower alkyl group;

X represents CO—$NR_3R_4$, $CH_2OH$, $CH_2OR_5$, $CH_2O$—$COR_6$, and $CH_2$—$NR_3R_4$, where $R_3$ and $R_4$ independently are H or lower alkyl, $R_5$ is lower alkyl of 1 to 6 carbons, and $R_6$ is lower alkyl of 1 to 6 carbons, carbocyclic aryl or heterocyclic aryl; or carbocyclic aryl or heteroaryl substituted lower alkyl group, and n is an integer between 0 and 8.

In another aspect the present invention relates to pharmaceutical compositions containing as active ingredient one or more compounds of the present invention (or their pharmaceutically acceptable salts).

In still another aspect the present invention relates to methods of administering to a mammal a pharmaceutical composition having as its active ingredient one or more compounds of Formula 1 (or their pharmaceutically acceptable salts) for the purpose of lowering intraocular pressure in the eye of the mammal.

DETAILED DESCRIPTION OF THE INVENTION

General Embodiments

The present invention relates to novel compounds of Formula 1, and to their use in pharmaceutical compositions and methods for the purpose of lowering intraocular pressure in the eye of a mammal.

Definitions

In Formula 1 as well as in all other chemical formulas in the present application for United States letters patent, bonds shown with hashed lines indicate α a bond below the plane of the paper, thus signifying configuration; bonds shown as a solid triangle indicate a bond above the plane of the paper, thus signifying β configuration; a dashed or dotted line represents a single bond or absence of a bond, and wavy lines attached to a double bond indicate that the configuration of substituents about the double bond can be cis or trans. Trans (E) configuration of substituents about a double bond is indicated by bonds pointing in opposite directions about a double bond, whereas cis (Z) configuration of substituents about a double bond is indicated by bonds pointing in the same direction about a double bond.

The term alkyl refers to and covers any and all groups which are known as normal alkyl, branch-chain alkyl and cycloalkyl. Lower alkyl means the above-defined broad definition of alkyl groups having 1 to 6 carbons, and as applicable, 3 to 6 carbons for branch chained and cyclo-alkyl groups.

4

The term "ester" as used here refers to and covers any compound falling within the definition of that term classically used in organic chemistry. Where the ester is derived from a carboxylic acid corresponding to Formula 1, the term covers the products derived from the treatment of this function with alcohols, preferably with aliphatic alcohols having 1–6 carbons. Where the ester is derived from alcohols corresponding to Formula 1, the term covers compounds of the formula —CH—OOCR$_2$ where $R_2$ is lower alkyl, carbocyclic aryl, heteroaryl, or carbocyclic aryl or heteroaryl substituted lower alkyl group.

Amide has the meaning classically accorded that term in organic chemistry. In this instance it includes but is not limited to unsubstituted amides and aliphatic mono-and di-substituted amides.

A pharmaceutically acceptable salt may be prepared for any compound used in the method of treatment of this invention, if the compound has a functionality capable of forming such salt, for example an acid functionality. A pharmaceutically acceptable salt may be any salt which retains the activity of the parent compound and does not impart any deleterious or untoward effect on the subject to which it is administered and in the context in which it is administered.

Such a salt may be derived from any organic or inorganic acid or base. The salt may be a mono or polyvalent ion. Of particular interest where the acid function is concerned are the inorganic ions, sodium, potassium, calcium, and magnesium. Organic amine salts may be made with amines, particularly ammonium salts such as mono-, di- and trialkyl amines or ethanol amines. Salts may also be formed with caffeine, tromethanine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri-acid may also be used.

The compounds of the present invention contain at least one double bond and therefore have trans and cis (E and Z) isomers. In addition, the compounds of the present invention contain one or more chiral centers and therefore exist in enantiomeric and diastereomeric forms. Unless the structural formula or the language of this application specifically designate a particular cis or trans isomer or a particular configuration of a chiral center, the scope of the present invention is intended to cover all such isomers per se, as well as mixtures of cis and trans isomers, mixtures of diastereomers and racemic mixtures of enantiomers (optical isomers) as well.

For the sake of ease of description, the side chain in Formula 1 which contains the 7-carbon side chain is sometimes referred to in the application as the "α side chain", and the other side chain attached to the cyclopentane or cyclopentene ring in accordance with Formula 1 is sometimes called as the "Ω side chain". This nomenclature is similar to the nomenclature used in naming the side chains of related prostaglandin compounds.

General Description of the Preferred Compounds of the Invention

Referring now to the structure shown in Formula 1, and regarding the olephinic bond in the α side chain, in the preferred compounds this olephinic bond is in the cis (Z) configuration.

With respect to the group $R_1$ on the Ω side chain of the compounds of the invention, $R_1$ is preferably H or CO—$R_2$ where a $R_2$ is lower alkyl, still more preferably lower alkyl of 1 to 3 carbons. With respect to the group X, compounds are preferred where X is $CH_2OH$, $CH_2OCH_3$, $CH_2OCO$-t-butyl, and where X is $CO-NH_2$, or $CO-NR_3SR_4$ where one of $R_3$ and $R_4$ is isopropyl, or where both $R_3$ and $R_4$ are methyl.

The most preferred compounds of the invention are identified below with reference to Formula 2.

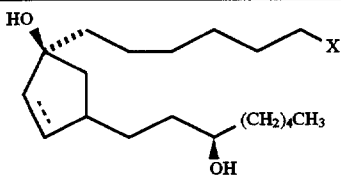

Formula 2

| COMPOUND # | "dashed line" represents | X |
|---|---|---|
| 1 | absence of a bond | $CH_2OH$ |
| 2 | absence of a bond | $CONH_2$ |
| 3 | absence of a bond | $CONH-CH(CH_3)_2$ |
| 4 | absence of a bond | $CON(CH_3)_2$ |
| 5 | a bond | $CH_2OH$ |
| 6 | a bond | $CH_2OCH_3$ |
| 7 | a bond | $CH_2OCO-C(CH_3)_3$ |
| 8 | a bond | $CONH_2$ |
| 9 | a bond | $CONH-CH(CH_3)_2$ |
| 10 | a bond | $CON(CH_3)_2$ |
| 11 | a bond | $CH_2N(CH_3)_2$ |

Methods of Administration, Formulations

Pharmaceutical compositions may be prepared by combining a therapeutically effective amount of at least one compound according to the present invention, or a pharmaceutically acceptable salt thereof, as an active ingredient, with conventional ophthalmically acceptable pharmaceutical excipients, and by preparation of unit dosage forms suitable for topical ocular use. The therapeutically efficient amount typically is between about 0.0001 and about 5% (w/v), preferably about 0.001 to about 1.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional, pharmaceutically acceptable preservatives, stabilizers and surfactants.

Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar vein, an ophthalmically acceptable antioxidant for use in the present invention includes, but is not limited to, sodium metabisulfite, sodium thiosulfate, acetylcysteine, butylated hydroxyanisol and butylated hydroxytoluene.

Other excipient components which may be included in the ophthalmic preparations are chelating agents. The preferred chelating agent is edentate disodium, although other chelating agents may also be used in place or in conjunction with it.

The ingredients are usually used in the following amounts:

| Ingredient | Amount (% w/v) |
|---|---|
| active ingredient | about 0.001–5 |
| preservative | 0–0.10 |
| vehicle | 0–40 |
| tonicity adjustor | 0–10 |
| buffer | 0.01–10 |
| pH adjustor | q.s. pH 4.5–7.5 |
| antioxidant | as needed |
| surfactant | as needed |
| purified water | as needed to make 100% | present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses.

Especially preservative-free solutions are often formulated in non-resealable containers containing up to about ten, preferably up to about five units doses, where a typical unit dose is from one to about 8 drops, preferably one to about 3 drops. The volume of one drop is about 20–35 μl.

Biological Activity

The ability of a pharmaceutical composition which contains a compound of Formula 1 to lower intraocular pressure in the eye of a mammal, can be demonstrated by an assay performed on the eyes of dogs. The assay is descibed as follows: male and female beagle dogs weighing 10–15 kg had been trained for a minimum of 2 months so that intraocular pressure could be measured without the use of restraining devices. Intraocular pressure was measured by pneumatonometry using applanation tonometers (Alcon). One minute prior to tonometry, 25 μl of proparacaine (Allergan, Irvine Calif.) was applied to minimize ocular discomfort during the procedure. Determination of the effects of the compounds of the invention on intraocular pressure involved administration of 1 to 25 μl of solution of the compound to one eye and an equal volume of vehicle to the contralateral eye as a control.

The effect of the compounds of the invention to lower intraocular pressure in dog eyes, in accordance with the above-described assay is shown in Table 1 with respect to the following compounds:

TABLE 1

| Compound # | Concentration % | Change in IOP 6 hours after administr. |
|---|---|---|
| 1 | 0.1 | −6.0 |
| 2 | 0.1 | −4.4 |
| 3 | 0.1 | −3.5 |
| 4 | 0.1 | −4.3 |
| 5 | 0.1 | −4.8 |
| 7 | 0.1 | −2.4 |
| 8 | 0.1 | −6.2 |
| 11 | 0.1 | −2.5 |

General Description of Synthetic Procedures

The compounds of the invention can be made by a number of different synthetic chemical pathways. To illustrate the invention, the following detailed description is provided. The synthetic chemist will readily appreciate that the conditions set out here are specific embodiments which can be generalized to obtain any and all compounds described in the present specification.

Reaction Scheme 1

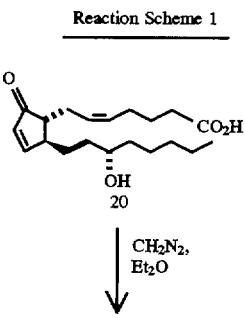

-continued
Reaction Scheme 1

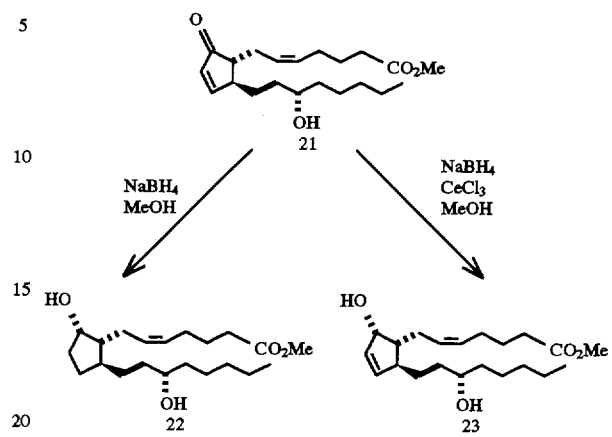

Referring now to Reaction Scheme 1, the compound 7α-[2-oxo-5β-(3α-hydroxyl-1-trans-octenyl)-3-cyclopentenyl]-5-cis-heptenoic acid (Compound 20) serves as a starting material. Compound 20 is also known as prostaglandin $A_2$, and is available commercially (Cayman Chemical Co., Ann Arbor, Mich.). Compound 20 is methylated by reaction with diazomethane in diethyl ether (or by some other known esterification procedure) to provide methyl 7α-[2-oxo-5β-(3α-hydroxyl-1-trans-octenyl)-3-cyclopentenyl]-5-cis-heptenoate (Compound 21). The "enone" function of Compound 21 is reduced with sodium borohydride to provide the alcohol compound (Compound 22) where the cyclopentane ring is saturated. The oxo portion of the "enone" function of Compound 21 is also reduced selectively with sodium borohydride in the presence of cerium trichloride to provide compound where the alicyclic ring retains the unsaturation.

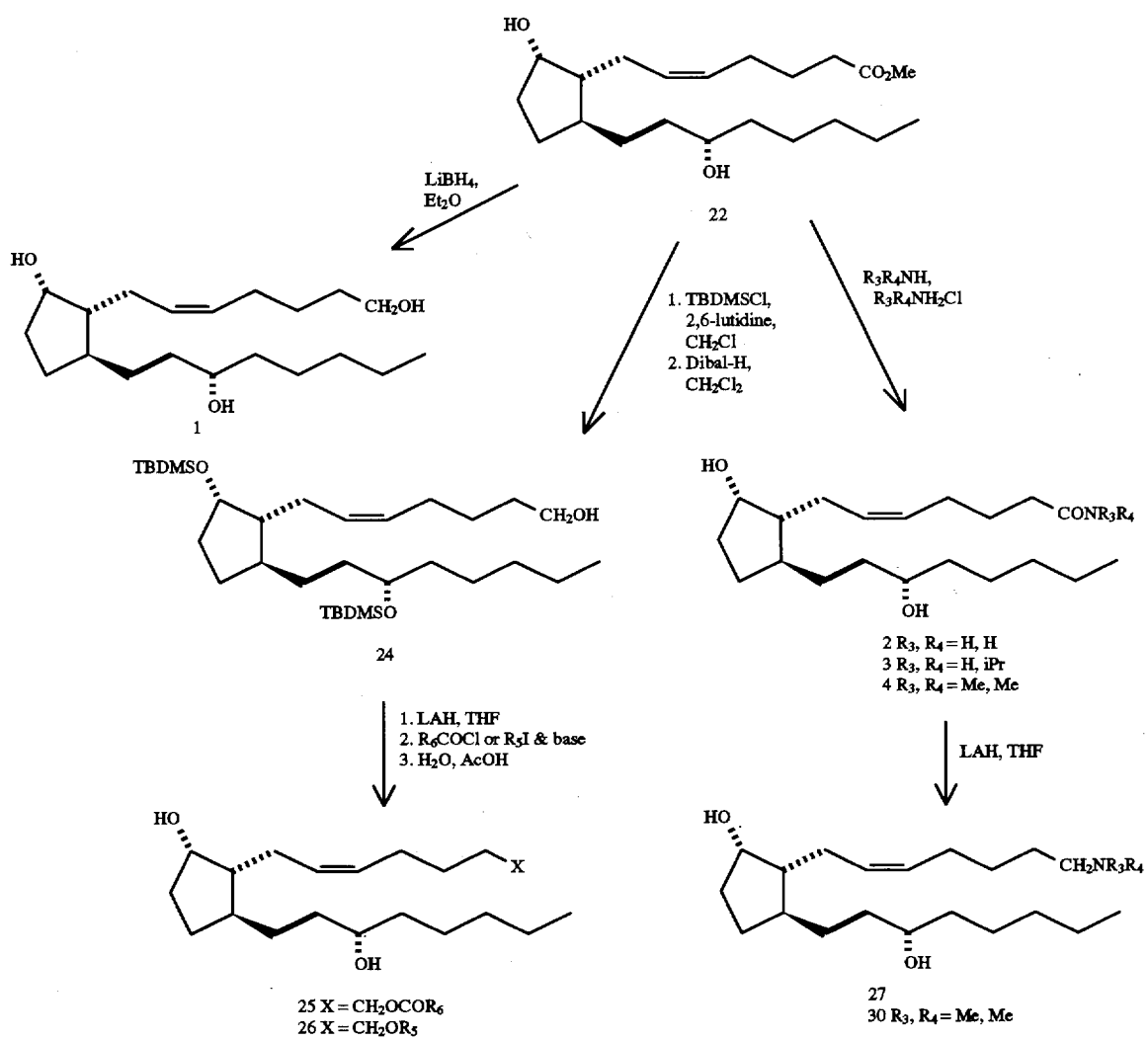

Reaction Scheme 2

Referring now to Reaction Scheme 2, the heptenoate ester function of Compound 22 is reduced with lithium borohydride, or by other suitable reducing agent, to provide the primary alcohol, Compound 1. Compound 1 is a biologically active compound in accordance with the present invention.

In order to obtain ester or ether derivatives of Compound 1, that is to obtain compounds where with reference to Formula 1 X is $CH_2OR_5$ or $CH_2O$—$COR_6$, the reduction of the heptenoate ester function is performed on the derivative (Compound 24) where the hydroxyl functions are protected by t-butyldimethylsilyl or other suitable protecting groups. Compound 24 can be obtained, for example, by reaction of Compound 22 with t-butyldimethylsilyl chloride in 2,6-lutidine. After reduction of Compound 24 the primary alcohol function can be esterified by reagents normally used for this purpose (such as an acyl chloride $R_6COCl$) or converted into an ether, (for example into an alkyl ether by reaction with an alkyl iodide $R_5$-I) whereafter the t-butyldimethylsilyl groups (or other suitable protecting groups) are removed from the secondary hydroxyl groups of the molecule to yield the ester (Compound 25) or ether (Compound 26).

To obtain compounds of the invention where the a side chain terminates with a carboxamide function (that is to obtain compounds where with reference to Formula 1 X is CO—$NR_3R_4$) Compound 22 is reacted with an amine and ammonium salt of the formula $R_3R_4NH$, $R_3R_4NH$ HCl. When the reagent is ammonia and ammonium chloride then the resulting compound is the unsubstituted amide (Compound 2); when the reagent is N-isopropylamine, N-isopropylamine hydrochloride, then the resulting compound is the isopropylamide (Compound 3), and when the reagent is N,N-dimethylamine and N,N-dimethylamine hydrochloride, then the resulting compound is the dimethylamide (Compound 4). The carboxamides obtained in the just described manner (such as Compounds 2, 3 and 4) are reduced with lithium aluminum hydride (or other suitable reducing agent) to provide the amine compounds of Formula 27.

Reaction Scheme 3

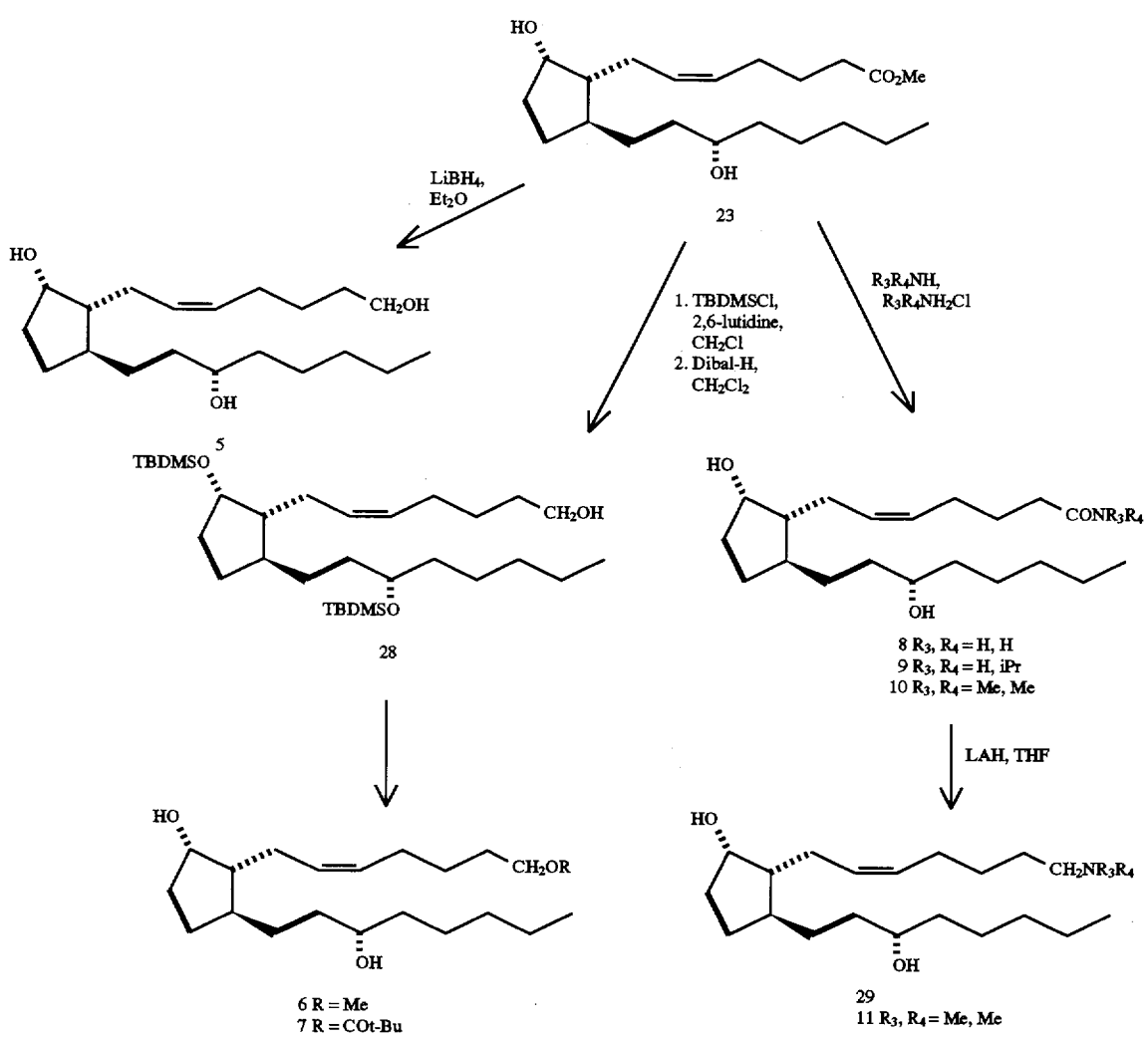

Referring now to Reaction Scheme 3, methyl 7α-[2α-hydroxyl-5β-(3α-hydroxyl-1-trans-octenyl)-3-cyclopentenyl]-5-cis-heptenoate (Compound 23) which is obtained in accordance with Reaction Scheme 1, serves as the starting material. The heptenoate ester function of Compound 23 is reduced with lithium borohydride to provide the corresponding primary alcohol (Compound 5). Ether and ester derivatives of the primary alcohol (heptanol) function are obtained in analogy to the similar reaction steps described in connection with Reaction Scheme 2. Thus the two secondary hydroxyl functions of Compounds 23 are first protected by reaction with t-butyldimethylsilylchloride or with t-butyldimethylsilyl trifluoromethane sulfonate, and thereafter the heptenoate ester function is reduced with diisobutylaluminum hydride (or other suitable reducing agent) to provide Compound 28. Compound 28 has a free primary alcohol group while the secondary alcohol groups are protected. Therefore Compound 28 can be acylated or converted into an ether with reactions well known in the art for this purpose. (See Reaction Scheme 2 for analogous reactions). The t-butyldimethylsilyl groups are removed by treatment with aqueous acid, to yield ether or ester derivatives of the primary alcohol function. Compound 6 is an example of the foregoing, where the primary alcohol has been converted into a methyl ether, and Compound 7 is an example where the primary alcohol is esterified by a t-butanoic (pivalic) acid residue.

Reaction of Compound 23 with ammonia and ammonium chloride, or with an amine of the formula $R_3R_4NH$ and the corresponding hydrochloride salt, yields the carboxamide compounds of the invention, that is compounds where with reference to Formula 1 X is $CO—NR_3R_4$. Thus, when the reagent is ammonia and ammonium chloride then the resulting compound is the unsubstituted amide (Compound 8); when the reagent is N-isopropylamine, N-isopropylamine hydrochlodide, then the resulting compound is the isopropylamide (Compound 9), and when the reagent is N,N-dimethylamine and N,N-dimethylamine hydrochloride, then the resulting compound is the dimethylamide (Compound 10). Reduction of the carboxamides, such as Compounds 8, 9, and 10, with lithium aluminum hydride (or other suitable reducing agents) results in compounds of the invention where the α side chain is a heptenylamine, of the general structure of Formula 29.

Compounds of the invention where the 3α-hydroxyl group of the Ω side chain is esterified (that is compounds where with reference to Formula 1 $R_1$ is $CO—R_2$) are obtained by esterification of the "free" 3α-hydroxyl compounds by reactions with an acid chloride ($R_2COCl$), dimethylaminopyridine catalyzed reaction with a carboxlic acid anhydride (($R_2$—CO)$_2$O), or reaction with an acid ($R_2$—COOH) in dimethylaminopyridine, or other esterification reactions known in the art. These reagents or reactions preferentially esterify the 3α-hydroxyl group over the hydroxyl group attached to the cyclopentane or cyclopentene ring. In the event a mixture of esters is obtained, the desired 3α-hydroxyl ester can be isolated, for example, by chromatography. Compounds of the invention where the 3α-hydroxyl group is esterified, and the α side chain includes a free heptenol moiety (that is compounds where with reference to Formula 1 $R_1$ is CO—$R_2$, and X is $CH_2OH$) are obtained from the corresponding heptenols (such as Compound 28) by first protecting the primary alcohol (heptenol) function with a suitable protecting group, such as the acid labile tetrahydropyranyl group. The t-butyldimethylsilyl groups are then removed from the secondary hydroxyl group by treatment with tetrabutylammonium fluoride, the 3α-hydroxyl group is preferentially acylated (as described above), and the tetrahydropyranyl protecting group is removed by mild acid treatment.

Compounds of the invention where the olefinic bond of the α side chain is in the trans configuration are obtained by isomerisation of the compounds of the invention through irradiation with U. V. light (for approximately 4 hours) in toluene as a solvent, in the presence of phenyldisulfide and 2,2'-azobisisobutyronitrile (AIBN). Preferably, intermediates such as Compound 24, are isomerized where the heptenoic acid or heptinol function and the secondary hydroxyl groups are protected.

SPECIFIC EXAMPLES

Methyl 7α-[2-oxo-5β-(3α-hydroxyl1-trans-octenyl)-3-cyclopentenyl]-5-cis-heptenoate (Compound 21)

A solution of diazomethane in $Et_2O$ was added dropwise to a solution of 7α-[2-oxo-5β-(3α-hydroxyl-1-trans-octenyl)-α-3-cyclopentenyl]-5-cis-heptenoic acid (Compound 20, 2.0 g, 6.22 mmol) in $Et_2O$ (100 mL) at 0° C. until the solution remained bright yellow. The reaction was allowed to warm to room temperature and was quenched with a few drops of acetic acid. The solvent was removed in vacuo to yield 2.0 g (93%) of the title compound as a clear, colorless oil: $^1H$ NMR (250 MHz, CDCl$_3$) δ 7.48 (dd, J=2.1, 4.8 Hz, 1H), 6.16 (dd, J=2.1, 4.8 Hz, 1H), 5.59–5.29 (m, 4H), 4.12–4.04 (m, 1H), 3.64 (s, 3H), 3.22–3.20 (m, 1H), 2.52–2.04 (m, 8H), 1.70–1.26 (m, 10H), 0.87 (t, J=5.5 Hz, 3H).

Methyl 7α-[2α-hydroxyl-5β-(3α-hydroxyl-1-trans-octenyl)-cyclopentyl]-5-cis-heptenoate (Compound 22)

Sodium tetrahydridoborate (154 mg, 4.07 mmol) was added to a solution of methyl 7α-[2-oxo-5β-(3α-hydroxyl-1-trans-octenyl)-3-cyclopentenyl]-5-cis-heptenoate (Compound 21, 1.77 g, 4.07 mmol) in methanol (16 mL) at 0° C. The reaction was allowed to warm to 23° C. and after 2 hours was quenched with saturated aqueous ammonium chloride. The solvent was removed in vacuo and the residue was diluted with $CH_2Cl_2$ (50 mL). The organic portion was separated, dried (Na$_2$SO$_4$), and concentrated in vacuo after filtration. Purification of the residue by flash column chromatography (silica gel, 3:1 hexane/EtOAc) afforded 1.70 g (98%) of a 1:1 mixture of α and β-cyclopentanols, which were separated by high pressure liquid chromatography (HPLC). $^1H$ NMR (250 MHz, CDCl$_3$) for the title compound (α-alcohol): δ 5.48–5.30 (m, 4H), 4.21–4.17 (m, 1H), 4.07–4.00 (m, 1H), 3.64 (s, 3H), 2.38–1.86 (m, 9H), 1.71–1.26 (m, 15H), 0.87 (t, J=5.8 Hz, 3H).

Methyl 7α-[2α-hydroxyl-5β-(3α-hydroxyl-1-trans-octenyl)-3-cyclopentenyl]-5-cis-heptenoate (Compound 23)

A solution of the methyl 7α-[2-oxo-5β-(3α-hydroxyl-1-trans-octenyl)-3-cyclopentenyl]-5-cis-heptenoate (Compound 21, 1.36 mg, 3.23 mmol) in methanolic cerium trichloride heptahydrate (8.1 mL of a 0.4M solution in MeOH, 3.23 mmol) was treated with sodium tetrahydridoborate (122 mg, 3.23 mmol) at 0° C. The reaction was allowed to warm to 23° C., stirred for 2 hours, and was then quenched with saturated aqueous ammonium chloride (2.0 mL). The resultant mixture was extracted with $CH_2Cl_2$ (2 X) and the combined organics were dried (Na$_2$SO$_4$), filtered and the filtrate concentrated in vacuo. Purification of the residue by flash column chromatography (silica gel, 3:1 hexane/EtOAc) afforded 1.22 g (89%) of a 1:1.5 mixture of α and β cyclopentanols which were separated by HPLC. $^1H$ NMR (250 MHz, CDCl$_3$) for the title compound (α-alcohol): δ 5.95–5.85 (m, 2H), 5.55–5.32 (m, 4H), 4.65–4.61 (m, 1H), 4.06–4.01 (m, 1H), 3.64 (s, 3H), 3.05–2.99 (m, 1H), 2.32–2.06 (m, 7H), 1.77–1.23 (m, 12H), 0.87 (t, J=5.8 Hz, 3H).

7α-[2α-hydroxyl5β-3α-hydroxyl-1-trans-octenyl)-cyclopentyl]-5-cis-heptenol (Compound 1)

Lithium tetrahydridoborate (0.177 mmol) was added to a solution of methyl 7α-[2α-hydroxyl-5β-(3α-hydroxyl-1-trans-octenyl)-cyclopentyl]-5-cis-heptenoate (Compound 22, 0.089 mmol) in $Et_2O$ (0.5 mL) at 23° C. After stirring for 1 hour the reaction was quenched with 2N NaOH and stirred for 0.5 h. The organic portion was separated and the aqueous layer was extracted with EtOAc. The combined organics were dried (MgSO$_4$), filtered and concentrated in vacuo. Purification of the residue by flash column chromatography (silica gel, 2:1 EtOAc/hex) afforded (82%) of title compound as a clear, colorless oil. $^1H$ NMR (250 MHz, CDCl$_3$): δ 5.49–5.40 (m, 4H), 4.25–4.21 (m, 1H), 4.07–4.03 (m, 1H), 3.65 (t, J=5.3 Hz, 2H), 2.41–1.89 (m, 7H), 1.68–1.27 (m, 18H), 0.88 (t, J=5.5 Hz, 3H).

7α-[2α-Hydroxyl-5β-(3α-hydroxyl-1-trans-octenyl)-cyclopentyl]-5-cis-heptenoic acid amide (Compound 2)

Ammonia gas (≈4 mL) was condensed into a tube containing methyl 7α-[2α-hydroxyl-5β-(3α-hydroxyl-1-trans-octenyl)-cyclopentyl]-5-cis-heptenoate (Compound 22, 57.8 mg, 0.130 mmol) and ammonium chloride (70 mg, 1.30 mmol). The tube was sealed and heated to 75° C. for 48 hours. The tube was then cooled to −70° C., vented and allowed to slowly warm to room temperature. The residue was diluted with saturated ammonium chloride and extracted with EtOAc. The organic portion was dried (MgSO$_4$), filtered and concentrated in vacuo. Purification of the residue by flash column chromatography (silica gel, 9:1 $CH_2Cl_2$/MeOH) afforded 45 mg (99%) of the title compound as an amorphous solid. $^1H$ NMR (250 MHz, CDCl$_3$): δ 6.10 (br s, 2H), 5.47–5.29 (m, 4H), 4.20–4.16 (m, 1H), 4.07–4.00 (m, 1H), 2.58 (br s, 2H), 2.35–1.87 (m, 9H), 1.72–1.22 (m, 13H), 0.85 (t, J=5.8 Hz, 3H).

7α-[2α-Hydroxyl-5β-(3α-hydroxyl-1-trans-octenyl)-cyclopentyl]-5-cis-heptenoic acid N-isopropylamide (Compound 3)

Methyl 7α-[2α-hydroxyl-5β-(3α-hydroxyl-1-trans-octenyl)-cyclopentyl]-5-cis-heptenoate (Compound 22, 70 mg, 0.16 mmol) was converted to the title compound in 72% yield using N-isopropylamine and N-isopropylamine hydrochloride according to the procedure described above for the unsubstituted amide (Compound 2). ¹H NMR (250 MHz, CDCl₃): δ 5.78 (br s, 1H), 5.47–5.27 (m, 4H), 4.20–4.17 (m, 1H), 4.06–4.00 (m, 2H), 2.31–1.87 (m, 13H), 1.72–1.26 (m, 13H), 1.12 (d, J=5.5 Hz, 6H), 0.85 (t, J=5.8 Hz, 3H).

7α-[2α-Hydroxyl-5β-(3α-hydroxyl-1-trans-octenyl)-cyclopentyl]-5-cis-heptenoic acid N, N-dimethylamide (Compound 4)

Methyl 7α-[2α-hydroxyl-5β-(3α-hydroxyl-1-trans-octenyl)-cyclopentyl]- 5-cis-heptenoate (Compound 22, 71 mg, 0.16 mmol) was converted to the title compound in 80% yield using N,N-dimethylamine and N,N-dimethylamine hydrochloride according to the procedure described above for the unsubstituted amide (Compound 2). ¹H NMR (250 MHz, CDCl₃): δ 5.48–5.36 (m, 4H), 4.19–4.16 (m, 1H), 4.07–4.02 (m, 1H), 2.95 (s, 6H), 2.40–1.83 (m, 12H), 1.71–1.27 (m, 12H), 0.86 (t, J=5.5 Hz, 3H).

N,N-Dimethyl 7α-[2α-hydroxyl-5β-(3α-hydroxyl-1-trans-octenyl)-cyclopentyl]-5-cis-heptenylamine (Compound 30)

Lithium aluminum hydride (0.37 mL of a 1.0M solution in THF, 0.372 mmol) was added to a solution of 7α-[2α-hydroxyl-5β-(3α-hydroxyl-1-trans-octenyl)-cyclopentyl]-5-cis-heptenoic acid N,N-dimethylamide (Compound 4) in THF (0.19 mL) at 0° C. The reaction was allowed to warm to 23° C., stirred for 5 hours, and then recooled to 0° C. before quenching with methanol. The mixture was diluted with EtOAc and washed with H₂O and brine. The organic portion was dried (MgSO₄), filtered and concentrated in vacuo. Purification of the residue by flash column chromatography (silica gel, 9:1 CH₂Cl₂/MeOH) afforded 26 mg (79%) of the title compound as a clear, yellow oil. ¹H NMR (250 MHz, CDCl₃): δ 5.47–5.36 (m, 4H), 4.18–4.15 (m, 1H), 4.05–3.99 (m, 1H), 2.39–1.85 (m, 11H), 2.29 (s, 6H), 1.67–1.27 (m, 15H), 0.86 (t, J=5.5 Hz, 3H).

7α-[2α-hydroxyl-5β-(3α-hydroxyl-1-trans-octenyl)-3-cyclopentenyl]-5-cis-heptenol (Compound 5)

Methyl 7α-[2α-hydroxyl-5β-(3α-hydroxyl-1-trans-octenyl)-3-cyclopentenyl]-5-cis-heptenoate (Compound 23, 28 mg, 0.064 mmol) was converted to the title compound in 52% yield according to the procedure described above for the 7α-[2α-hydroxyl-5β-(3α-hydroxyl- 1-trans-octenyl)-cyclopentyl]-5-cis-heptenol (Compound 1). ¹H NMR (250 MHz, CDCl₃): δ 5.98–5.90 (m, 2H), 5.58–5.45 (m, 4H), 4.71–4.67 (m, 1H), 4.12–4.06 (m, 1H), 3.65 (t, J=5.3 Hz, 2H), 3.08–3.04 (m, 1H), 2.39–2.02 (m, 4H), 1.81–1.28 (m, 16H), 0.89 (t, J=5.8 Hz, 3H).

7α-[2α-Hydroxyl-5β-(3α-hydroxyl-1-trans-octenyl)-3-cyclopentenyl]-5-cis-heptenoic acid a amide (Compound 8)

Methyl 7α-[2α-hydroxyl-5β-(3α-hydroxyl-1-trans-octenyl)-3-cyclopentenyl]-5-cis-heptenoate (Compound 23, 59 mg, 0.135 mmol) was converted to the title compound in 32% yield according to the procedure described above for the unsubstituted amide (Compound 2). ¹H NMR (250 MHz, CDCl₃): δ 5.95–5.31 (m, 8H), 4.63–4.58 (m, 1H), 4.07–4.03 (m, 1H), 3.05–2.98 (m, 1H), 2.31–1.78 (m, 7H), 1.75–1.18 (m, 10H), 0.86 (t, J=5.8 Hz, 3H).

7α-[2α-Hydroxyl-5β-(3α-hydroxyl-1-trans-octenyl)-3-cyclopentenyl]-5-cis-heptenoic acid N-isopropylamide (Compound 9)

Methyl 7α-[2α-hydroxyl-5β-(3α-hydroxyl-1-trans-octenyl)-3-cyclopentenyl]-5-cis-heptenoate (Compound 23, 53 mg, 0.122 mmol) was converted to the title compound in 66% yield using N-isopropylamine and N-isopropylamine hydrochloride according to the procedure described above for the unsubstituted amide (Compound 2).

¹H NMR (250 MHz, CDCl₃): δ 5.95–5.86 (m, 2H), 5.59–5.36 (m, 5H), 4.65–4.63 (m, 1H), 4.09–3.99 (m, 2H), 3.06–3.01 (m, 1H), 2.39–2.02 (m, 6H), 1.78–1.24 (m, 13H), 1.12 (d, J=5.5 Hz 3H), 1.11 (d, J=5.5 Hz, 3H), 0.87 (t, J=4.5 Hz, 3H).

7α-[2α-Hydroxyl-5β-(3α-hydroxyl-1-trans-octenyl)-3-cyclopentenyl]-5-cis-heptenoic acid N,N-dimethylamide (compound 10)

Methyl 7α-[2α-hydroxyl-5β-(3α-hydroxyl-1-trans-octenyl)-3-cyclopentenyl]-5-cis-heptenoate (Compound 23, 70 mg, 0.161 mmol) was converted to the title compound in 74% yield using, N,N-dimethylamine and N, N-dimethylamine hydrochloride according to the procedure described above for the unsubstituted amide (Compound 2). ¹H NMR (250 MHz, CDCl₃): δ 5.95–5.86 (m, 2H), 5.51–5.35 (m, 4H), 4.64–4.61 (m, 1H), 4.06–4.02 (m, 1H), 3.05–3.01 (m, 1H), 2.96 (s, 3H), 2.91 (s, 3H), 2.38–2.09 (m, 7H), 1.78–1.23 (m, 12H), 0.86 (t, J=5.5 Hz, 3H).

N,N-Dimethyl 7α-[2α-hydroxyl-5β-(3α-hydroxyl-1-trans-octenyl)-3-cyclopentenyl]-5-cis-heptenylamine (Compound 11)

7α-[2α-Hydroxyl-5β-(3α-hydroxyl-1-trans-octenyl)-3-cyclopentenyl]-5-cis-heptenoic acid N,N-dimethylamide (Compound 10, 24 mg, 0.066 mmol) was converted to the title compound in 34% yield according to the procedure described above for N,N-dimethyl 7α-[2α-hydroxyl-5β-(3α-hydroxyl-1-trans-octenyl)-cyclopentyl]-5-cis-heptenylamine (Compound 30). ¹H NMR (250 MHz, CDCl₃): δ 5.96–5.86 (m, 2H), 5.53–5.33 (m, 4H), 4.64–4.62 (m, 1H), 4.05–3.98 (m, 1H), 3.05–3.01 (m, 1H), 2.38–2.01 (m, 7H), 2.18 (s, 6H), 1.75–1.26 (m, 14H), 0.86 (t, J=5.8 Hz, 3H).

7α-[2α-t-butyldimethylsilyloxy-5β-(3α-t-butyldimethyl-silyloxy-1-trans-octenyl)-3-cyclopentenyl]5-cis-heptenol (compound 28)

A solution of methyl 7α-[2α-hydroxyl-5β-(3α-hydroxyl-1-trans-octenyl)-3-cyclopentenyl]-5-cis-heptenoate (Compound 23, 142 mg, 0.326 mmol), 2,6-lutidine (0.17 mL, 1.30 mmol) and t-butyldimethylsilyl trifluoromethanesulfonate (0.30 mL, 1.30 mmol) in CH₂Cl₂(0.65 mL) was stirred at 23° C. for 16 hours. The reaction was quenched with saturated aqueous sodium bicarbonate and extracted with CH₂Cl₂. The organic portion was washed with 10% aq. citric acid, saturated aq. sodium bicarbonate, and brine. After drying over anhydrous Na₂SO₄ the organic portion was filtered and concentrated in vacuo to yield the bis-TBDMS ether as a yellow oil.

The bis-TBDMS ether was diluted with CH₂Cl₂, cooled to 0° C., and diisobutylaluminum hydride (2.45 mL of a 1.0M solution in CH₂Cl₂, 2.45 mmol) was added dropwise. After stirring for 1 hour the reaction was quenched with 1N NaOH, stirred for 0.5 hour, and extracted with CH₂Cl₂. The organic portion was dried (Na₂SO₄), filtered and concentrated in vacuo. Purification of the residue by flash column chromatography (silica gel, 9:1 hex/EtOAc) afforded 61 mg (79%) of the title compound as a clear, colorless oil. Characteristic peaks at δ 3.62 ppm (t, J=5.3 Hz, 2H, CH₂OH) and δ 0.86 ppm (s, 9H, SiC(CH₃)₃ and δ 0.85 ppm (s, 9H, SiC(CH₃)₃.

Methyl 7α-[2α-hydroxyl-5β-(3α-hydroxyl-1-trans-octenyl)-3-cyclopentenyl]-5-cis-heptenyl ether
(Compound 6)

To a suspension of sodium hydride (4.0 mg, 0.168 mmol) in DMF (0.11 mL) cooled to 0° C. was added 7α-[2α-t-butyldimethylsilyloxy-5β-(3α-t-butyldimethyl-silyloxy-1-trans-octenyl)-3-cyclopentenyl]-heptenol (Compound 28, 31 mg, 0.056 mmol) in DMF (0.22 mL). After hydrogen evolution ceased iodomethane (16 μL, 0.252 mmol) was added and the reaction mixture was allowed to slowly warm to room temperature. The reaction was quenched with saturated aqueous ammonium chloride and extracted with $Et_2O$. The organic portion was dried ($MgSO_4$), filtered and concentrated in vacuo to yield a clear, colorless oil.

The crude bis-TBDMS methyl ether was diluted with THF (0.5 mL) and tetrabutylammonium fluoride (0.22 mL of a 1.0M solution in THF, 0.22 mmol) was added. The resultant solution was stirred for 16 hours at 23° C. and concentrated in vacuo. Purification of the residue by flash column chromatography (silica gel, 1:1 hex/EtOAc) afforded 11 mg (61%) of the title compound as a clear, colorless oil. $^1$H NMR (250 MHz, $CDCl_3$): δ 5.95–5.86 (m, 2H), 5.53–5.35 (m, 4H), 4.66–4.62 (m, 1H), 4.07–4.00 (m, 1H), 3.35 (t, J=5.5 Hz, 2H), 3.30 (s, 3H), 3.05–3.01 (m, 1H), 2.36–2.03 (m, 5H), 1.79–1.25 (m, 16H), 0.87 (t, J=4.5 Hz, 3H).

7α-[2αhydroxyl-5β-(3-hydroxyl-1-trans-octenyl)-3-cyclopentenyl]-5-cis-heptenyl pivalate
(Compound 7)

To a solution of 7α-[2α-t-butyldimethylsilyloxy-5β-(3α-t-butyldimethylsilyloxy-1-trans-octenyl)-3-cyclopentenyl]-5-cis-heptenol (Compound 28, 70 mg, 0.127 mmol) and pyridine (0.25 mL) in $CH_2Cl_2$ (0.25 mL) cooled to 0° C. was added trimethylacetyl chloride (32 μL, 0.254 m mol). The reaction was allowed to warm to room temperature, stirred for 6 hours, and then quenched with saturated aq. ammonium chloride. The organic portion was separated and washed with 1N HCl, saturated aq. sodium bicarbonate, brine and then dried ($Na_2SO_4$), filtered and concentrated in vacuo to afford a slightly yellow oil.

The crude bis-TBDMS pivalate was diluted with THF (0.5 mL) and tetrabutylammonium fluoride (0.50 mL of a 1.0M solution in THF, 0.50 mmol) was added. The resultant solution was stirred for 16 h at 23° C. and concentrated in vacuo. Purification of the residue by flash column chromatography (silica gel, 1:1 hex/EtOAc) afforded 33.7 mg (54%) of the title compound as a clear, colorless oil. $^1$H NMR (250 MHz, $CDCl_3$): δ 5.96–5.86 (m, 2H), 5.52–5.35 (m, 4H), 4.68–4.63 (m, 1H), 4.08–4.00 (m, 4H), 3.06–3.01 (m, 1H), 2.38–2.06 (m, 4H), 1.80–1.26 (m, 14H), 1.17 (s, 9H), 0.88 (t, J=5.5 Hz, 3H).

What is claimed is:

1. A compound of the formula

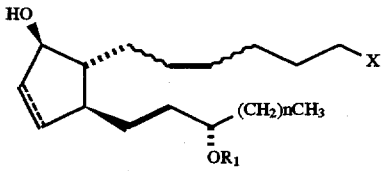

where the dotted line represents a bond or the absence of bond, the wavy lines represent bonds which are either in cis or trans configuration;

$R_1$ represents H, or CO—$R_2$ where $R_2$ is lower alkyl of 1 to 6 carbons, carbocyclic aryl or heterocyclic aryl; or carbocyclic aryl or heteroaryl substituted lower alkyl group;

X represents $CH_2$—$NR_3R_4$, where $R_3$ and $R_4$ independently are H or lower alkyl, and n is an integer between 0 and 8.

2. A compound of claim 1 where the dotted line represents a bond.

3. A compound of claim 1 where the dotted line represents absence of a bond.

4. A compound of claim 1 where the wavy lines attached to the olefinic bond represent that the olefinic bond is in the trans configuration.

5. A compound of claim 1 where n is 4.

6. A compound of the formula

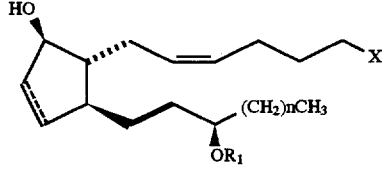

where the dotted line represents a bond or the absence of a bond;

$R_1$ represents H, or CO—$R_2$ where $R_2$ is lower alkyl of 1 to 6 carbons, carbocyclic aryl or heterocyclic aryl; or carbocyclic aryl or heteroaryl substituted lower alkyl group;

X represents $CH_2$—$NR_3R_4$, where $R_3$ and $R_4$ independently are H or lower alkyl, n is an integer between 0 and 8.

7. A compound of claim 6 wherein the dotted line represents absence of a bond.

8. A compound of claim 7 wherein n is 4.

9. A compound of claim 8 wherein $R_1$ is H.

10. A compound of claim 9 wherein $R_1$ is CO—$R_2$.

11. A compound of claim 6 wherein the dotted line represents absence of a bond.

12. A compound of claim 11 wherein n is 4.

13. A compound of claim 12 wherein $R_1$ is H.

14. A compound of claim 13 wherein $R_1$ is CO—$R_2$.

15. A compound of the formula

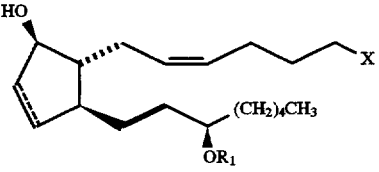

where the dotted line represents a bond or the absence of a bond;

$R_1$ represents H, or CO—$R_2$ where $R_2$ is lower alkyl of 1 to 6 carbons, and X represents $CH_2$—$NR_3R_4$, where $R_3$ and $R_4$ independently are H or lower alkyl.

16. A compound of claim 15 wherein $R_1$ is H.

17. A compound of claim 16 wherein the dotted line represents a bond and X is $CH_2N(CH_3)_2$.

18. A method for lowering intraocular pressure in the eye of a mammal, which comprises administering to the mammal a pharmaceutical composition containing a pharmaceutically acceptable excipient and an effective amount of a compound having the formula

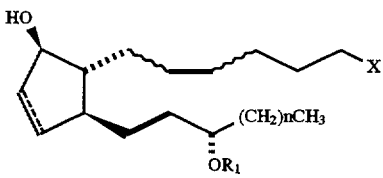

where the dotted line represents a bond or the absence of a bond, the wavy lines represent bonds which are either in cis or trans configuration;

$R_1$ represents H, or $CO-R_2$ where $R_2$ is lower alkyl of 1 to 6 carbons, carbocyclic aryl or heterocyclic aryl; or carbocyclic aryl or heteroaryl substituted lower alkyl group;

X represents $CH_2-NR_3R_4$, where $R_3$ and $R_4$ independently are H or lower alkyl, and n is an integer between 0 and 8.

19. The method of claim 18 wherein the pharmaceutical composition is adapted for topical administration.

* * * * *

UNITED STATES PATENT AND TRADEMARK OFFICE
CERTIFICATE OF CORRECTION

PATENT NO. : 5,674,910
DATED : October 7, 1997
INVENTOR(S) : Garst et al.

It is certified that error appears in the above-indentified patent and that said Letters Patent is hereby corrected as shown below:

Column 2, line 25, "uvecscleral" should be --uveoscleral--.
Column 3, line 50, after "indicate", delete "$\alpha$".
Column 3, line 51, after "signifying", add --$\alpha$--.
Column 4, line 67, after "where", delete "a".
Column 5, line 3, "CO-NR$_3$SR$_4$" should be --CO-NR$_3$R$_4$--.
Column 6, line 29, add the line --the actual dose of the active compounds of the--.
Column 8, line 41, "compound" should be --Compound--.
Column 8, line 41, after "compound", add --23--.
Column 10, line 47, "a" should be --$\alpha$--.
Column 13, line 2, "carboxlic" should be --carboxylic--.
Column 13, line 35, after "hydroxyl", add -- - --.
Column 14, line 27, after "hydroxyl", add -- - --.
Column 15, line 52, after "acid", delete "a".
Column 16, line 13, "(compound" should be --(Compound--.
Column 16, line 17, after "using", delete ",".
Column 16, line 42, "(compound" should be --(Compound--.
Column 17, line 8, after "-cyclopentenyl]", add -- -5-cis --.
Column 17, line 28, after "7$\alpha$-[2$\alpha$", add -- - --.
Column 17, line 28, after "-5$\beta$-(3", add --$\alpha$--.

UNITED STATES PATENT AND TRADEMARK OFFICE
CERTIFICATE OF CORRECTION

PATENT NO. : 5,674,910
DATED : October 7, 1997
INVENTOR(S) : Garst et al.

It is certified that error appears in the above-indentified patent and that said Letters Patent is hereby corrected as shown below:

Column 17, line 36, "m mol" should be --mmol--.
Column 17, line 66, before "bond", add --a--.
Column 2, line 3, "Postagladins" should be --Prostaglandins--.
Column 2, line 32, "hyptensive" should be --hypotensive--.
Column 2, line 35, "prostagladins" should be --prostaglandins--.
Column 2, line 40, "postaglandins" should be --prostaglandins--.
Column 4, line 56, after "called", delete "as".
Column 6, line 51, "descibed" should be --described--.
Column 11, line 54, "Compounds" should be --Compound--.
Column 12, line 55, "hydrochlodide" should be --hydrochloride--.
Column 13, line 30, "heptinol" should be --heptenol--.
Column 16, line 8, after "1.12 (d, J=5.5 Hz", add --,--.

Signed and Sealed this

Seventh Day of July, 1998

Attest:

*Attesting Officer*

BRUCE LEHMAN

*Commissioner of Patents and Trademarks*